(12) United States Patent
Fabbri (10) Patent No.: US 11,627,999 B2
(45) Date of Patent: Apr. 18, 2023

(54) CONVERTIBLE INTRAMEDULLARY FEMORAL NAIL AND USE THEREOF FOR MANAGEMENT OF METASTATIC CANCER TO BONE

(71) Applicant: Memorial Sloan Kettering Cancer Center, New York, NY (US)

(72) Inventor: Nicola Fabbri, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 17/059,912

(22) PCT Filed: Jun. 3, 2019

(86) PCT No.: PCT/US2019/035259
§ 371 (c)(1),
(2) Date: Nov. 30, 2020

(87) PCT Pub. No.: WO2019/232545
PCT Pub. Date: Dec. 5, 2019

(65) Prior Publication Data
US 2021/0259750 A1    Aug. 26, 2021

Related U.S. Application Data

(60) Provisional application No. 62/679,650, filed on Jun. 1, 2018.

(51) Int. Cl.
*A61B 17/72* (2006.01)
*A61B 17/88* (2006.01)

(52) U.S. Cl.
CPC ...... *A61B 17/7233* (2013.01); *A61B 17/8802* (2013.01)

(58) Field of Classification Search
CPC ............. A61B 17/72–7291; A61F 2/36–3676
See application file for complete search history.

(56) References Cited

U.S. PATENT DOCUMENTS

| 5,112,333 | A   |   | 5/1992 | Fixel |            |
|-----------|-----|---|--------|-------|------------|
| 5,902,340 | A   | * | 5/1999 | White | A61F 2/36  |
|           |     |   |        |       | 128/898    |
| 6,168,595 | B1  |   | 1/2001 | Durham et al. |    |
| 6,264,699 | B1  | * | 7/2001 | Noiles | A61F 2/40 |
|           |     |   |        |       | 623/23.23  |

(Continued)

FOREIGN PATENT DOCUMENTS

WO    WO-00/76414 A1    12/2000

OTHER PUBLICATIONS

International Search Report and Written Opinion, PCT/US2019/035259, Memorial Sloan Kettering Cancer Center (dated Oct. 1, 2019).

*Primary Examiner* — Eduardo C Robert
*Assistant Examiner* — Steven J Cotroneo
(74) *Attorney, Agent, or Firm* — Foley & Lardner LLP (57) ABSTRACT

Described herein is an intramedullary femoral nail implant. The implant can be more easily converted to a load bearing hip replacement. Fixation of the intramedullary nail may be enhanced by injection of cement. Disclosed devices may be preferable to other types of intramedullary nails at the time of the first procedure given their characteristics of improved fixation, stability, and flexibility for potential conversion via a less complex operation.

18 Claims, 6 Drawing Sheets

(56) References Cited

U.S. PATENT DOCUMENTS

| | | | | |
|---|---|---|---|---|
| 6,319,286 | B1* | 11/2001 | Fernandez | A61F 2/3609 |
| | | | | 623/23.18 |
| 7,273,499 | B2* | 9/2007 | McCleary | A61F 2/4607 |
| | | | | 623/18.11 |
| 9,237,949 | B2* | 1/2016 | Podolsky | A61F 2/4609 |
| 2001/0034523 | A1 | 10/2001 | Nelson | |
| 2002/0004685 | A1* | 1/2002 | White | A61F 2/36 |
| | | | | 623/23.15 |
| 2002/0133156 | A1* | 9/2002 | Cole | A61B 17/725 |
| | | | | 606/62 |
| 2003/0097184 | A1* | 5/2003 | Mitsugi | A61B 17/8841 |
| | | | | 623/23.19 |
| 2006/0084999 | A1 | 4/2006 | Aschmann | |
| 2012/0172992 | A1* | 7/2012 | Fockens | A61F 2/4014 |
| | | | | 623/19.13 |
| 2014/0276826 | A1 | 9/2014 | Metzinger et al. | |
| 2015/0190233 | A1* | 7/2015 | Link | A61F 2/367 |
| | | | | 623/23.42 |
| 2017/0035470 | A1 | 2/2017 | Pool et al. | |
| 2019/0053836 | A1* | 2/2019 | Sweeney | A61B 17/72 |
| 2019/0336186 | A1* | 11/2019 | Tanaka | A61B 17/7233 |
| 2020/0197188 | A1* | 6/2020 | Cavanagh | A61F 2/42 |
| 2021/0128205 | A1* | 5/2021 | Roche | A61B 17/8061 |

* cited by examiner

CONVERTIBLE INTRAMEDULLARY FEMORAL NAIL AND USE THEREOF FOR MANAGEMENT OF METASTATIC CANCER TO BONE

CROSS-REFERENCE TO RELATED APPLICATIONS

This application is a U.S. National Stage under 35 U.S.C. § 371 of International Application No. PCT/US2019/035259, filed on Jun. 3, 2019, which claims priority to U.S. Provisional Patent Application No. 62/679,650 entitled "CONVERTIBLE INTRAMEDULLARY FEMORAL NAIL AND USE THEREOF FOR MANAGEMENT OF METASTATIC CANCER TO BONE," filed Jun. 1, 2018, the disclosure of each of which is incorporated herein by reference in its entirety.

TECHNICAL FIELD

The present application relates generally to an intramedullary implant, and more specifically to a convertible intramedullary femoral nail well-suited for management of bone metastasis, and to the fixation and conversion of an intramedullary implant.

BACKGROUND

Prevalence of metastatic cancer to bone is underestimated and currently reported to be 300,000 cases in the United States. The femur in general, and the hip region in particular, is the most common location for metastatic cancer to bone. Surgical management of bone metastasis is usually considered for impending or actual pathologic fracture. Surgical implants include intramedullary nails, more frequently used, and hip prostheses, less commonly used. Most patients with femoral disease ultimately require surgical fixation. In the femur, the choice of internal fixation is usually limited to a long-stemmed hip arthroplasty or an intramedullary femoral nail. The choice is essentially between a load-bearing (prosthesis) and a load-sharing device (intramedullary nail). However, subsequent tumor relapse or occurrence of new metastasis may occur in the proximal region of the femur, requiring conversion of a nail into a hip replacement. Revision surgery of a nail for conversion to a hip prosthesis is usually complex and difficult. What are needed are systems, apparatuses, and methods that address one or more of the above, as well as other, shortcomings of conventional approaches.

SUMMARY

While the life expectancy of patients with bone cancer has increased over the last decade, so too has the risk of failure for load-sharing devices such as intramedullary nails. This is due in large part to subsequent tumor progression, recurrence, or occurrence of a new metastatic lesion in the proximal region of the femur or ipsilateral periacetabular region. In these circumstances, revision surgery of the nail and conversion to a hip hemiarthroplasty or total hip replacement may be necessary. This currently requires a long and complex procedure in patients that are frequently suboptimal surgical candidates because of poor performance and/or immunocompromised status, high risk of perioperative complications, and short life expectancy. Revision surgery in this setting includes removal of the previous nail and insertion of a hip prosthesis, and may last several hours and portend significant morbidity. In the alternative, a custom-made device, usually very expensive and requiring several weeks to be manufactured, can be utilized.

One aspect of the present disclosure is directed to a novel nail implant. In another aspect of the present disclosure, a nail implant that can more easily be converted into a load bearing hip replacement is disclosed. Yet another aspect of the present disclosure is directed to enhancing the fixation of an intramedullary nail by the injection of cement.

Various embodiments of the disclosure relate to an intramedullary fixation system. The intramedullary fixation system may comprise a proximal femoral replacement component, which may include a first opening, a first aperture, and a second aperture separated from the first aperture via the first opening. The intramedullary fixation system may comprise a nail component, which may be configured to be insertable within a medullary cavity of a bone. The nail component may extend from a first nail end portion to a second nail end portion. The second nail end portion may include a channel. The second nail end portion may be sized to be received within the first opening of the proximal femoral replacement component. The channel may be configured to be aligned with the first aperture and the second aperture of the proximal femoral replacement component when the second nail end portion is received within the first opening. The intramedullary fixation system may comprise a side locking fixation component. The side locking fixation component may extend from a first end portion to a second end portion. The second end portion may be configured to pass through the first aperture of the proximal femoral replacement component, the channel of the nail component, and the second aperture of the proximal femoral replacement component to secure the nail component to the proximal femoral replacement component.

In one or more embodiments, the second aperture of the proximal femoral replacement component may define an opening of a fixation component receiver, which may be configured to secure the second end portion of the side locking fixation component subsequent to the side locking fixation component passing through the first aperture of the proximal femoral replacement component, the channel of the nail component, and the second aperture of the proximal femoral replacement component.

In one or more embodiments, the fixation component receiver may extend from a receiver first end portion defining the second aperture to a second closed end portion.

In one or more embodiments, the proximal femoral replacement component may include a first chamber defined by the first opening at a first end portion of the first chamber and a first wall structure at a second end portion of the first chamber. The second aperture may be formed in the first wall structure. The fixation component receiver may extend from the second aperture in the first wall structure.

In one or more embodiments, the fixation component receiver may extend from the proximal femoral replacement component at an angle with respect to a longitudinal axis of the proximal femoral replacement component.

In one or more embodiments, the proximal femoral replacement component may further comprise a first end portion defining the first opening having a first longitudinal central axis and a second end portion defining a second opening having a second longitudinal central axis. The second longitudinal central axis may be eccentric with respect to the first longitudinal central axis.

In one or more embodiments, the proximal femoral replacement component may comprise a first chamber defined by the first opening at a first end portion of the first chamber and a first wall structure at a second end portion of the first chamber and including the second aperture. The proximal femoral replacement component may comprise a second chamber defined by a second opening at a first end portion of the second chamber and a second wall structure at a second end portion of the second chamber and including the first aperture. The first chamber and the second chamber may be in fluid communication via a passage extending from the first aperture to the second aperture.

In one or more embodiments, the second end portion of the first chamber may be joined to a first end portion of the second chamber at about a midsection of the proximal femoral replacement component.

In one or more embodiments, an intramedullary fixation system may comprise a fixation component receiver protruding from a sidewall of the proximal femoral replacement component. The fixation component receiver may extend from a receiver first end to a receiver second end. The fixation component receiver may be tapered from the receiver first end to the receiver second end.

In one or more embodiments, the nail component may include at least one opening extending through the first nail end portion of the nail component. The at least one opening may be configured to receive securing devices to secure the first nail end portion to an adjacent bone structure.

In one or more embodiments, the side locking fixation component may have an external diameter sized to match an internal diameter of a fixation component receiver extending from the proximal femoral replacement component.

In one or more embodiments, the second end portion of the side locking fixation component includes engagement features configured to engage with corresponding engagement features of a fixation component receiver extending from the proximal femoral replacement component.

In one or more embodiments, a length of the nail component is at least four times a length of the proximal femoral replacement component.

In one or more embodiments, a diameter of the first aperture and the second aperture of the proximal femoral replacement component may be at least four times less than a diameter of the first opening of the proximal femoral replacement component.

In one or more embodiments, the first opening of the proximal femoral replacement component may have a diameter that is greater than a diameter of the first aperture of the proximal femoral replacement component.

In one or more embodiments, the first end portion of the side locking fixation component may have a diameter greater than a diameter of the first aperture of the proximal femoral replacement component.

Various embodiments relate to a proximal femoral replacement component. The proximal femoral replacement component may comprise a first opening configured to receive a nail end portion of a nail component. The nail end portion may include a channel configured to be aligned with a first aperture and a second aperture when the nail end portion is received within the first opening. The second aperture may be separated from the first aperture via the first opening. The proximal femoral replacement component may be configured to receive a side locking fixation component, which may extend from a first end portion to a second end portion. The side locking fixation component may be configured to pass through the first aperture, the channel of the nail component, and the second aperture to secure the nail component to the proximal femoral replacement component.

In one or more embodiments, the proximal femoral replacement component may comprise a first end portion defining the first opening having a first longitudinal central axis and a second end portion defining a second opening having a second longitudinal central axis. The second longitudinal central axis may be eccentric with respect to the first longitudinal central axis.

In one or more embodiments, the proximal femoral replacement component may comprise a first chamber defined by the first opening at a first end portion of the first chamber and a first wall structure at a second end portion of the first chamber and including the second aperture. The proximal replacement component may comprise a second chamber defined by a second opening at a first end portion of the second chamber and a second wall structure at a second end portion of the second chamber and including the first aperture. The first chamber and the second chamber may be in fluid communication via a passage extending from the first aperture to the second aperture.

In one or more embodiments, the second aperture may define an opening of a fixation component receiver, which may be configured to secure the second end portion of the side locking fixation component subsequent to the side locking fixation component passing through the first aperture of the proximal femoral replacement component, the channel of the nail component, and the second aperture of the proximal femoral replacement component.

In one or more embodiments, the proximal femoral replacement component may include a first chamber defined by the first opening of the proximal femoral replacement component at a first end portion of the first chamber and a first wall structure at the second end portion of the first chamber, the second aperture being formed in the first wall structure. The fixation component receiver may extend from the second aperture in the first wall structure.

In one or more embodiments, a diameter of the first aperture and the second aperture may be at least four times greater than a diameter of the first opening. A length of the nail component may be at least four times as great as a length of the proximal femoral replacement component.

In one or more embodiments, a diameter of the first aperture may be less than a diameter of the first end portion of the side locking fixation component.

Example devices disclosed herein may be preferable to other types of intramedullary nails at the time of the first procedure given their characteristics of improved fixation, stability, and flexibility for potential conversion via a less complex operation.

Various embodiments relate to a method for implanting intramedullary nails using an intramedullary fixation system. The method may comprise:

accessing, by an incision, a medullary canal at a first end portion of a bone;

inserting, via the medullary canal from the first bone end portion to a distance from a second bone end portion, a nail component extending from a first nail end portion to a second nail end portion, the second nail end portion including a channel;

determining the alignment of the channel of the second nail end portion respective to a first aperture and a second aperture of a proximal femoral replacement component;

aligning, subsequent to determining the alignment of the channel, the channel of the second nail end portion respective to the first aperture and the second aperture of the proximal femoral replacement component;

inserting, via the medullary canal at the first bone end portion, the proximal femoral replacement component including the first opening and the first aperture and the second aperture separated from the first aperture via the first opening;

encapsulating, by the proximal femoral replacement component, the second nail end portion; and inserting, via a portion of the bone corresponding to the channel and the first aperture and the second aperture, a side locking fixation component through the first aperture of the proximal femoral replacement component, the channel of the nail component, and the second aperture of the proximal femoral replacement component to lock the proximal femoral replacement component and the nail component to the bone.

These and other features of various embodiments can be understood from a review of the following detailed description in conjunction with the accompanying drawings.

It is to be understood that both the foregoing general description and the following detailed description and accompanying drawings are exemplary and explanatory and are not restrictive of the present invention, as claimed.

BRIEF DESCRIPTION OF THE FIGURES

The foregoing and other objects, aspects, features, and advantages of the disclosure will become more apparent and better understood by referring to the following description taken in conjunction with the accompanying drawings, in which.

DETAILED DESCRIPTION

Following below are more detailed descriptions of various concepts related to, and embodiments of, inventive systems, devices, apparatuses, products, and methods for intramedullary nails and use thereof. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

In example embodiments of the disclosure, a proximal femoral replacement component can slide on a well-fixed nail and can be secured with a side locking bolt and cement, based on pre-designed features of the nail.

In example embodiments of the disclosure, a gun-activated cement injector, having a thin flexible nozzle, allows for distal femoral injection to maximize or otherwise enhance bone fixation. The cement mixer may be a standard or quasi-standard cement injector that uses a long tube for distal injection in the femur, to help guarantee better nail fixation and behavior as load-bearing device.

Referring to FIGS. 1A, 1B, 1C, 1D, 1E, and 1F, an intramedullary implant 100 may include a proximal femoral replacement component 110, a nail component 150 which may be forced into the medullary cavity of a bone (not shown), and a side locking bolt 180 as a fixation component. The nail component 150 extends from a distal nail end 155 to a proximal nail end 160, which includes a nail bolt aperture 165. The proximal femoral replacement component 110 may include a main opening 115 into which the proximal nail end 160 of the nail component 150 is inserted. The proximal femoral replacement component 110 may also include bolt apertures 120a/120b, and a bolt sleeve or receiver 125 with an opening sized to receive therein at least a portion of the side locking bolt 180.

To secure the nail component 150 to the proximal femoral replacement component 110, the proximal nail end 160 slides into the main opening 115 of the proximal femoral replacement component 110 so as to substantially align the central axis of the bolt aperture 120a/120b (e.g., a central axis extending between apertures 120a and 120b) with the central axis of the nail bolt aperture 165. The side locking bolt 180 may then be inserted into the bolt aperture 120a/120b in the proximal femoral replacement component 110, through the nail bolt aperture 165, into the bolt aperture 120b, and into the bolt receiver 125. The nail component 150 is then restricted from being retracted or otherwise pulled out of the proximal femoral replacement component 110 by side locking bolt 180. The bolt receiver 125 (or an inner wall thereof) may be tapered such that when the side locking bolt 180 is received therein, the side locking bolt 180 friction fits in the bolt receiver 125.

The proximal femoral replacement component 110 can include at least the main opening 115 and the bolt apertures 120a/120b. The proximal femoral replacement component 110 can be composed of at least one biocompatible material, such as silicone, polyethylene, titanium, polylactic acid, ceramic, stainless steel, cobalt chrome, carbon fiber, composite materials such as reinforced plastic, resorbable material, or a combination thereof. The main opening 115 can be referred to as a first opening 115 of the proximal femoral replacement component 110. The main opening 115 can have a diameter of, for example, 15 millimeters ("mm"), 20 mm, or 23 mm, which can reflect the diameter of the proximal nail end 160 of the nail component 150. The diameter of the main opening 115 can be sized to pass a portion of the proximal nail end 160 of the nail component 150. The proximal femoral replacement component 110 can have a length of, for example, 5 centimeters ("cm"), 10 cm, or 12 cm corresponding to a parameter of a bone structure, such that the proximal femoral replacement component 110 can be engaged between at least two bone structures. For example, the proximal femoral replacement component 110 can have a length that allows it to engage a portion of a pelvis and a portion of the femur to secure the intramedullary implant 100.

The proximal femoral replacement component 110 can also include a cement opening 120 at an opposing end of the proximal femoral replacement component 110 from the main opening 115. The main opening 115 and the cement opening 130 can provide access to introduce a passage 195 (see FIG. 1F) of the proximal femoral replacement component 110. The passage 195 can be configured to receive and enclose at least a portion of the nail component 150 within the proximal femoral replacement component 110. The passage 195 can be circular, rectangular, equilateral, or equiangular in shape to mate with the proximal nail end 160. In some embodiments, the passage 195 can be tapered to provide a friction fit with the nail component 150 for additional security. For example, the proximal nail end 160 of the nail component 150 can be inserted into the main opening 115 and can travel through the passage 195, which friction fits the proximal nail end 160 of the nail component 150 with the proximal femoral replacement component 110.

In some other embodiments, the proximal femoral replacement component 110 does not have the bolt receiver 125 such that, for example, the passage 195 secures the proximal nail end 160 of the nail component 150 to the proximal femoral replacement component 110 without use of the side locking bolt 180. The passage 195 can be configured with at least a groove. The groove can be spiraled wherein, for example, the nail component 150 can be secured within the proximal femoral replacement component 110 by inserting the nail component 150 via the main opening 115 and through a portion of the passage 195, and twisting the nail component 150 to lock the said component within the proximal femoral replacement component 110.

The proximal femoral replacement component 110 can include a first aperture 120*a* and a second aperture 120*b*. The bolt receiver 125 can be referred to as, and used interchangeably with, other descriptive terms such as a bolt sleeve. The bolt apertures 120*a*/120*b* can be formed by drilling holes in the proximal femoral replacement component 110. The bolt apertures 120*a*/120*b* can have diameters of, for example, 7 mm, 10 mm, or 12 mm which can be less than the diameter of the main opening 115. In some cases, the diameter of the bolt aperture 120*a*/120*b* can be, for example, at least three times, four times, or five times less than the diameter of the main opening 115. The first aperture 120*a* can be separated from the second aperture 120*b* by the main opening 115 of the proximal femoral replacement component 110, such that the side locking bolt 180 can travel via the first aperture 120*a*, to the first opening 115, and then to the second aperture 120*b* in a subsequent order. The second aperture 120*b* can include a diameter similar to the first aperture 120*a*, such that the side locking bolt 180 can be inserted via the first aperture 120*a* and/or the second aperture 120*b* interchangeably. In some embodiments, the first aperture 120*a* can include a diameter greater than or less than the second aperture 120*b* such that the path of side locking bolt 180 narrows after the side locking bolt 180 is inserted. For example, the diameter of the second aperture 120*b* can be configured to be less than the diameter of the first aperture 120*a* to friction fit the side locking bolt 180, wherein the side locking bolt 180 can be inserted through the first aperture 120*a*, traveling through the nail bolt aperture 165 of the nail component 150, and being received at the second aperture 120*b*.

In some embodiments, the second aperture 120*b* can include at least one engagement feature to secure the side locking bolt 180. The engagement feature can include, for example, a groove (not shown), wherein the groove can be at least a spiral, a socket, or a latch to secure the side locking bolt 180 with the second aperture 120*b* via a twist or turn motion by the locking bolt 180. The engagement feature can be provided for faster engagement or disengagement of the said bolt to easily replace component(s). In some cases, the engagement feature can be a friction fitting, such that the side locking bolt 180 can be secured or fastened by the first aperture 120*a* and/or the second aperture 120*b* enclosure of the proximal femoral replacement component 110.

In some embodiments, the proximal femoral replacement component 110 can include the bolt receiver 125. The bolt receiver 125 can be referred to as and used interchangeably with the descriptive term fixation component receiver 125. The bolt receiver 125 can be, for example, 5 cm, 10 cm, or 12 cm long, capable of engaging to at least a portion of, for example, the pelvis. The bolt receiver 125 can have a length greater than the length of the side locking bolt 180. The bolt receiver 125 can extend out from the proximal femoral replacement component 110, with the second aperture 120*b* as an opening into the bolt receiver 125. The bolt receiver 125 can be tapered to friction fit the side locking bolt 180 into the bolt receiver 125 to secure the nail component 150 to the proximal femoral replacement component 110, subsequent to the side locking bolt 180 passing via the first aperture 120*a*, the nail bolt aperture 165 of the nail component 150, and the second aperture 120*b*.

In some embodiments, the bolt receiver 125, protruding from the wall of the proximal femoral replacement component 110, can be angled with respect to a longitudinal axis of the proximal femoral replacement component 110. The longitudinal axis of the proximal femoral replacement component 110 can refer to a direction of the said component 110, such as north, south, east, west, or between therein. The bolt receiver 125 can be angled, for example, 120 degrees, 130 degrees, 145 degrees, or residing between 90 degrees and 180 degrees with respect to the main opening 115 of the proximal femoral replacement component 110. The bolt receiver 125 can be angled to adjoint, for example, the femur with at least a portion of the pelvis, wherein the femur is in contact with the pelvis at the angle said for the bolt receiver 125.

The nail component 150, extending from the distal nail end 155 to the proximal nail end 160, can include at least the nail bolt aperture 165 situated at the proximal nail end 160. The distal nail end 155 and the proximal nail end 160 can be referred to as a first nail end portion 155 and a second nail end portion 160 of the nail component 150 respectively, wherein the said end portion can refer to a distance from an end of the nail component 150, such as 10 mm, 20 mm, or 30 mm from the end of the nail component 150. The nail component 150 can be composed or constructed with at least one biocompatible material, which can be similar to the proximal femoral replacement component 110 material(s). The nail component 150 can include a length such as 27 cm, 30 cm, or 36 cm, which can correspond to the length of, for example, the femur as to align a plurality of portions of the femur. The length of the nail component 150 can be, for example, three times, four times, or five times the length of the proximal femoral replacement component 110. The length of the nail component 150 can correspond to, for example, the length of the femur for alignment. The nail component 150 can further include a diameter similar to the diameter of the main opening 115. The nail component 150 can be hollow to reduce composition or construction material, as well as the weight of the nail component 150.

In some embodiments, the nail component 150 (or the proximal nail end portion 160) can be tapered such that the proximal nail end 160 include a diameter greater than the distal nail end 155 diameter. The distal nail end portion 155 of the tapered nail component 150 can include a diameter of, for example, 7 mm, 10 mm, or 12 mm for insertion of the nail component 150 into a portion of the bone structure, such as the femur. In some other embodiments, the nail component 150 can be isometric extending from the distal nail end 155 to the proximal nail end 160 if, for example, the diameter of the main opening 115 is sized to accommodate for the diameter of the said bone structure.

The nail bolt aperture 165 can be situated a distance from the proximal end of the nail bolt aperture 165. The nail bolt aperture 165 can be referred to as and used interchangeably with other descriptive terms, such as channel or passage. The nail bolt aperture 165 of the nail component 150 can include a diameter less than the diameter of the proximal nail end 160 and/or the main opening 115, for example, 6 mm, 9 mm, or 13 mm. The nail bolt aperture 165 can be configured to align with the first aperture 120a and the second aperture 120b of the proximal femoral replacement component 110. The diameter of the nail bolt aperture 165 can be similar to the diameter of the side locking bolt 180 to allow the side locking bolt 180 to slide from the first aperture 120a of the proximal femoral replacement component 110, pass the nail bolt aperture 165, and to the second aperture 120b of the proximal femoral replacement component 110. The diameter of the nail bolt aperture 165 can be further sized to correspond with the first aperture 120a and the second aperture 120b of the proximal femoral replacement component 110. The nail bolt aperture 165, extending through the proximal nail end 160, can be tapered to accommodate a difference in diameter of the first aperture 120a and the second aperture 120b. In some cases, the nail bolt aperture 165 extending through the proximal nail end 160 can be angled to align with the bolt aperture 120a/120b of the proximal femoral replacement component 110, wherein the bolt receiver 125 can be angled with respect to a first wall structure 187 (further discussed below).

In some embodiments, the nail component 150 can include a second nail bolt aperture 157 extending through the distal nail end 155 portion of the nail component 150. The second nail bolt aperture can have a diameter less than or substantially equal to the nail bolt aperture 165 diameter. The second nail bolt aperture can be configured to receive or pass a securing device, like the side locking bolt 180, to an adjacent bone structure. For example, subsequent to inserting the nail component 150 into the femur from a first end to the second end of the femur, the securing device can be inserted through the adjacent bone structure portion, a distance from the second end of the femur, to secure the distal nail end 155 of the nail component 150 to the femur. The second nail bolt aperture can be circular, rectangular, or another geometrical shape corresponding to the shape of the securing device.

The side locking bolt 180 can be referred to as and used interchangeably with other descriptive terms such as a side locking fixation component 180. The side locking bolt 180 can be defined as an extension from a first end portion 181 to a second end portion 182, wherein the end portions refer to opposing ends of the side locking bolt 180. The side locking bolt 180 can be composed of at least one biocompatible material, which can be similar to the proximal femoral replacement component 110 material(s). The side locking bolt 180 can include an exterior diameter of, for example, 7 mm, 10 mm, or 12 mm, which can be similar to the interior diameter of the first aperture 120a and the second aperture 120b of the proximal femoral replacement component 110, and the nail bolt aperture 165 of the nail component 150. The side locking bolt 180 can have a length, for example, 5 cm, 10 cm, or 12 cm, to engage between a portion of the bone structure at the first end portion and the second aperture 120b of the proximal femoral replacement component 110 at the second end portion.

The side locking bolt 180 can include an extension 127, with a second, smaller diameter, residing at the second end portion. In some versions, having a smaller diameter allows extension 127 to fit through second aperture, whereas the remainder of the side locking bolt 180 does not fit. The extension 127 can include a diameter less than the first end portion such that the extension 127 can be configured to friction fit with the bolt receiver 125. In some cases, the first end portion diameter can be greater than the diameter of the first aperture 120a of the proximal femoral replacement component 110, such that the first end of the side locking bolt 180 does not intrude the proximal femoral replacement component 110. For example, the side locking bolt 180 can be configured to pass the second end portion of the side locking bolt 180 through the first aperture 120a of the proximal femoral replacement component 110 subsequent to the nail component 150 being inserted into the proximal femoral replacement component 110. The side locking bolt 180 (or the extension 127 thereof) can be further inserted through the nail bolt aperture 165 of the nail component 150, and to the second aperture 120b of the proximal femoral replacement component 110 in a subsequent order to secure the nail component 150 to the proximal femoral replacement component 110.

In some embodiments, the second end portion of the side locking bolt 180 can include at least one engagement feature. The engagement feature can be configured to engage the side locking bolt 180 with the second aperture 120b of the proximal femoral replacement component 110, which can be the bolt receiver 125, wherein the second aperture 120b includes a corresponding engagement feature.

Figure 1A:
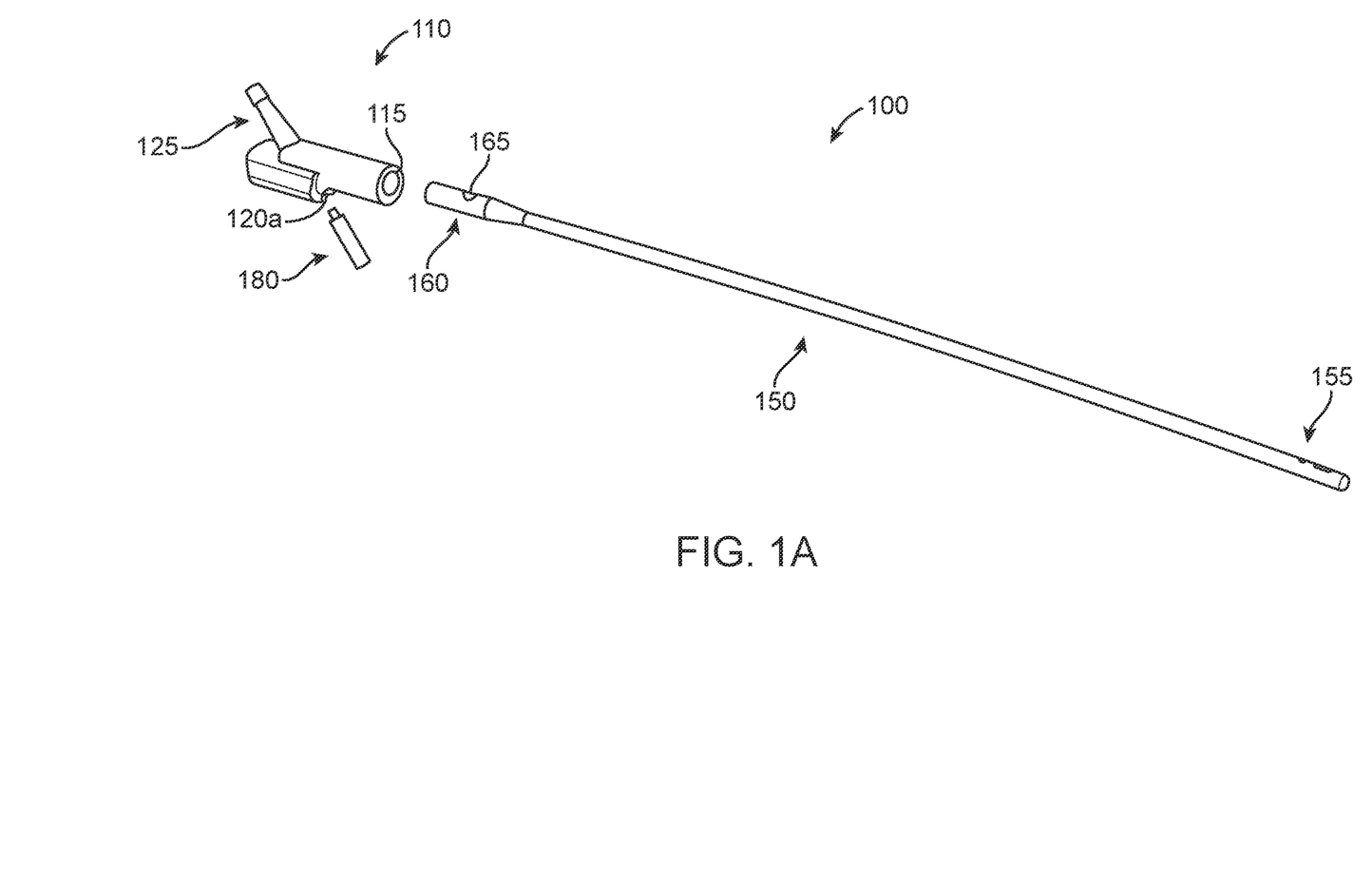
FIG. 1A provides a perspective view of an intramedullary implant in accordance with one or more example embodiments.
Figure 1B:
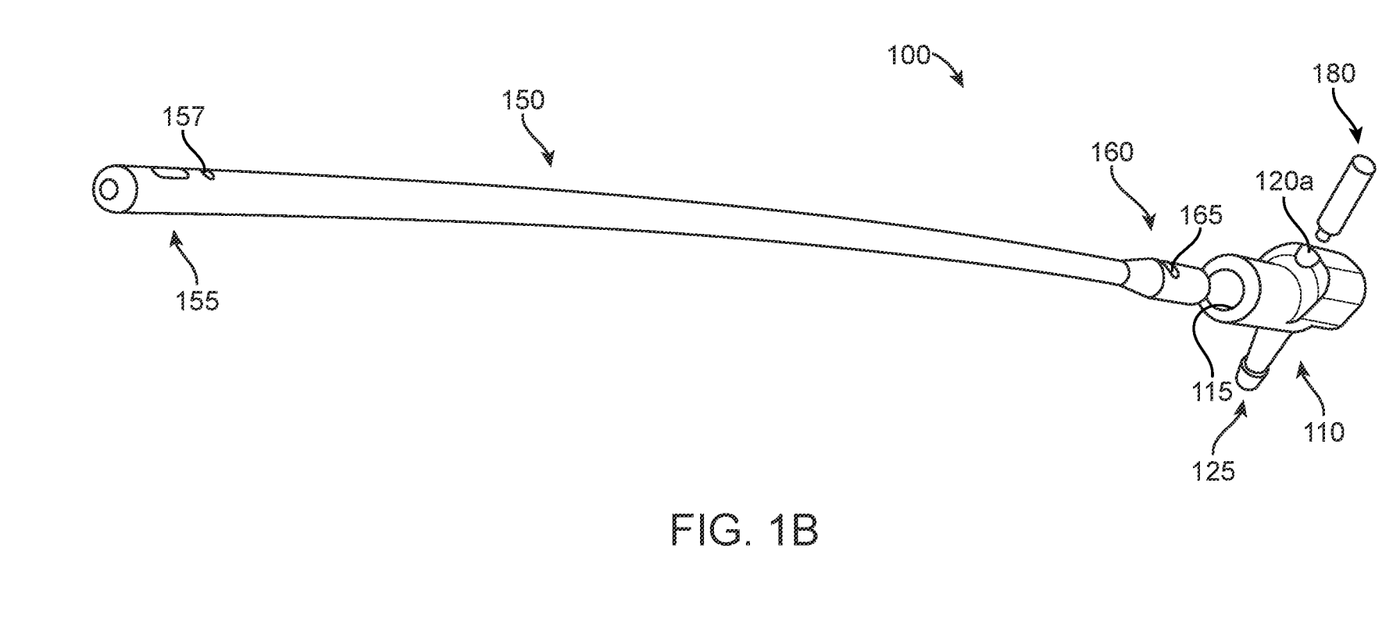
FIG. 1B provides an alternative perspective view of the intramedullary implant of FIG. 1A in accordance with one or more example embodiments.
Figure 1C:
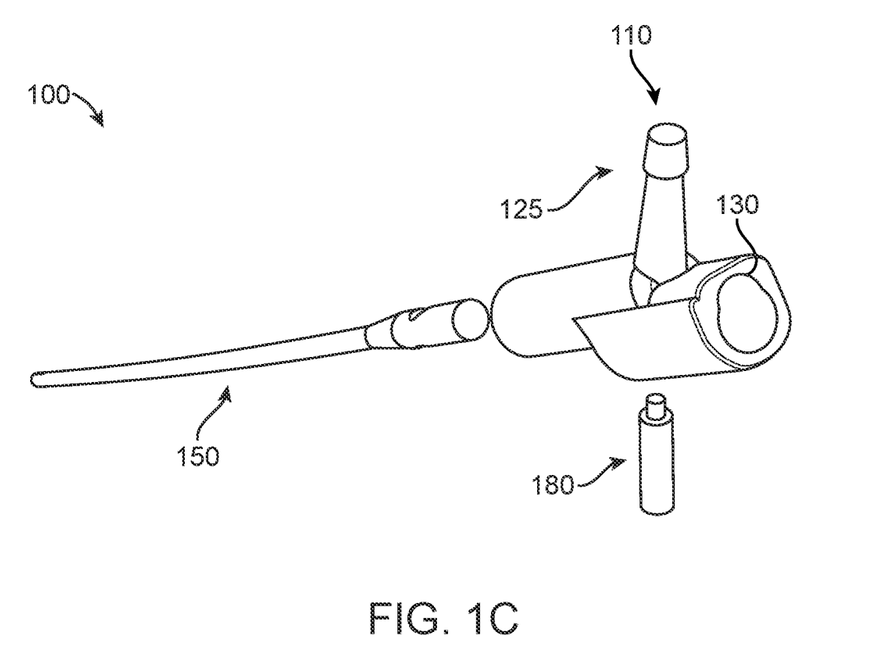
FIG. 1C provides an alternative perspective view of the intramedullary implant of FIGS. 1A and 1B in accordance with one or more example embodiments.
Figure 1D:
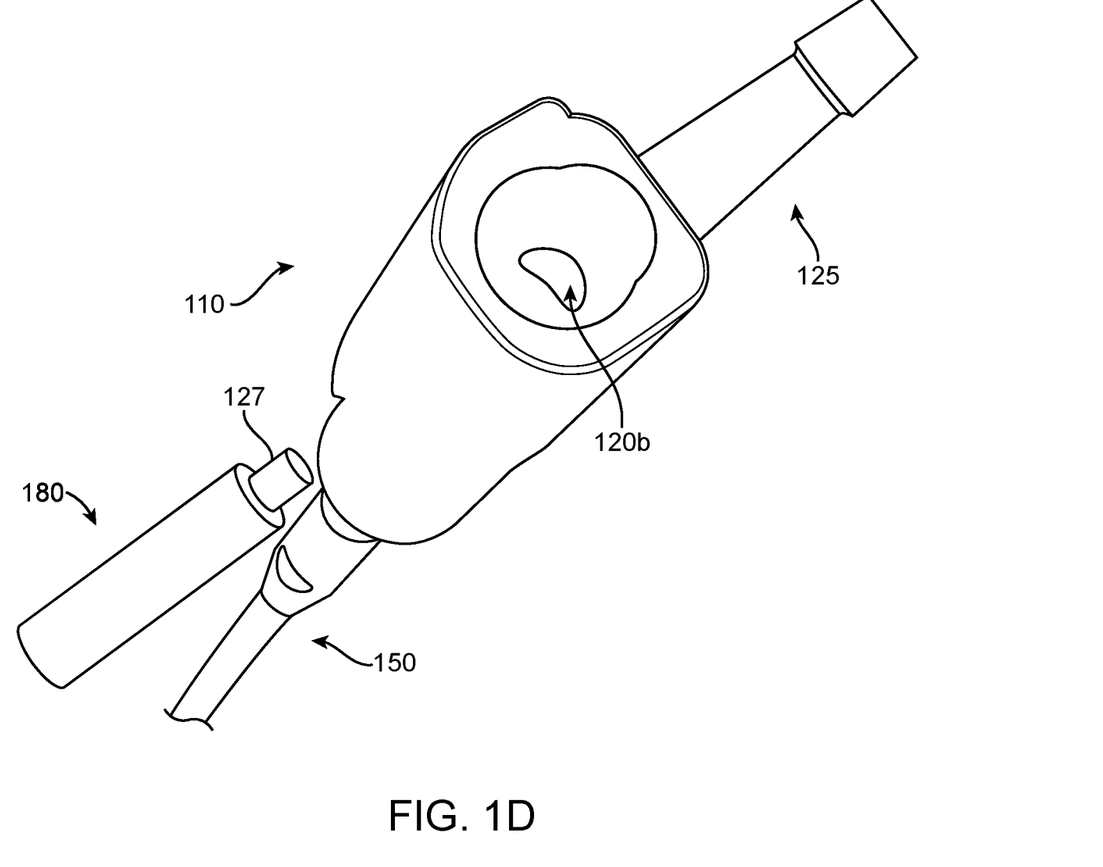
FIG. 1D provides an alternative perspective view of the intramedullary implant of FIGS. 1A, 1B, and 1C, in accordance with one or more example embodiments.
Figure 1E:
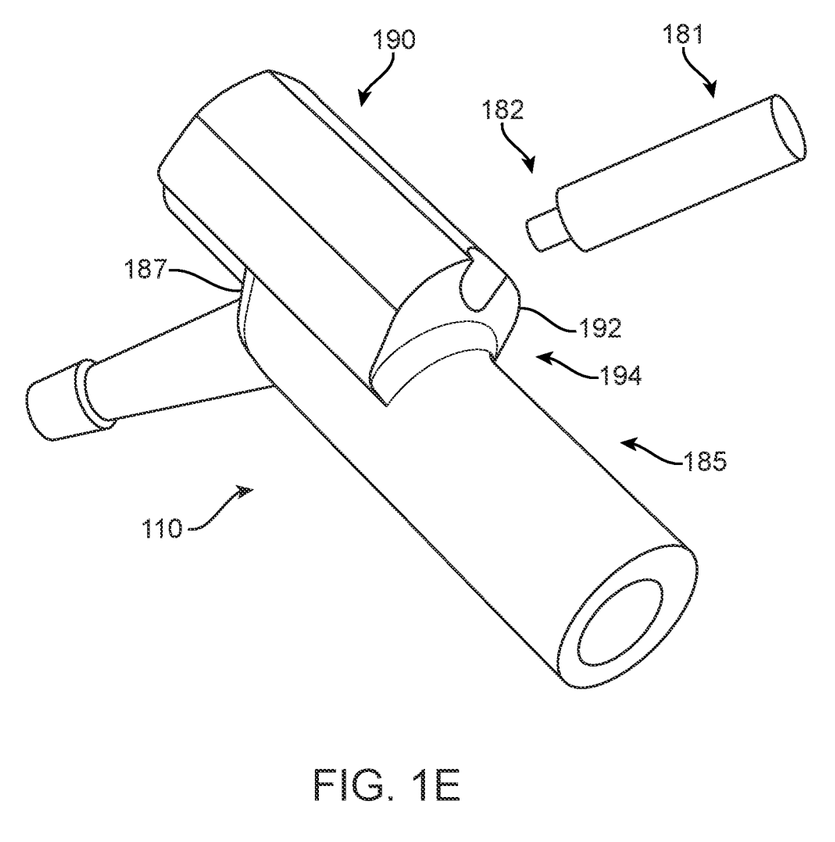
FIG. 1E provides an alternative perspective view of a proximal femoral replacement component of the intramedullary implant of FIGS. 1A, 1B, 1C, and 1D, in accordance with one or more example embodiments.
Figure 1F:
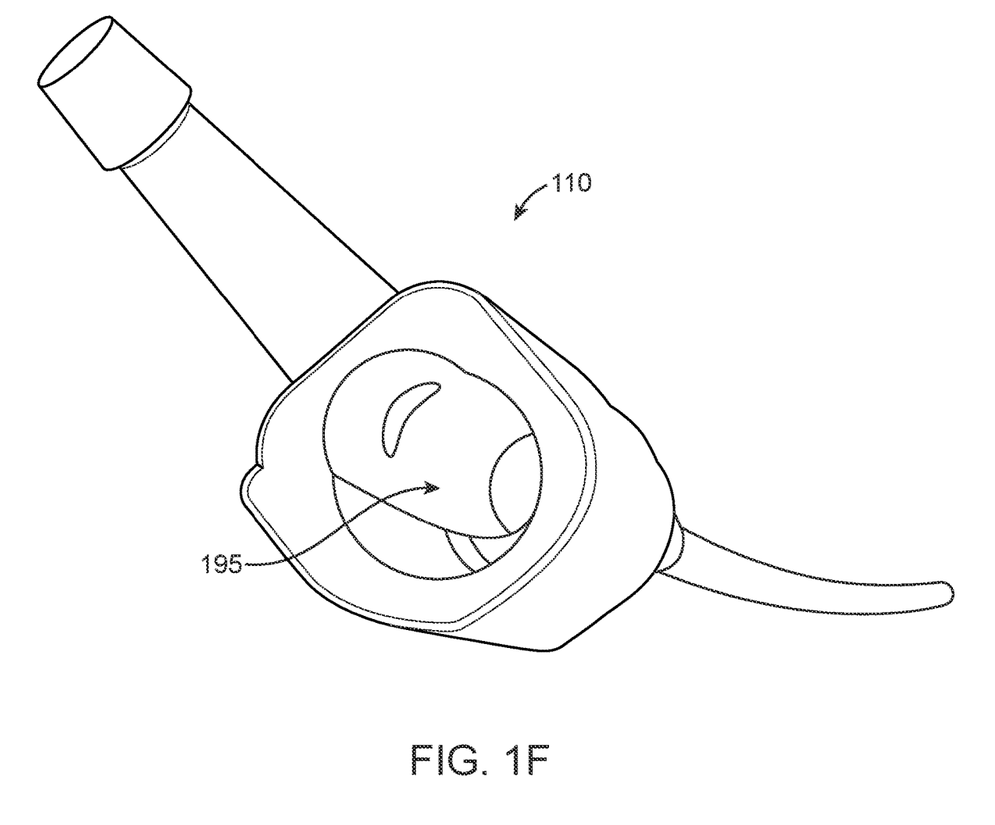
FIG. 1F provides an alternative perspective view of the intramedullary implant of FIGS. 1A, 1B, 1C, 1D, and 1E, in accordance with one or more example embodiments.

Referring more specifically to FIG. 1C and FIG. 1E, the proximal femoral replacement component 110 additionally includes a cement opening 130, a first wall structure 187, a second wall structure 192, and a midsection 194 where the first wall structure 187 and the second wall structure 192 meet. The cement opening 130 can be referred to as a second opening into a second end portion of the proximal femoral replacement component 110, and the main opening 115 can be referred to as the first opening 115 into a first end portion of the proximal femoral replacement component 110. An end of a nozzle of a cement injector may be inserted into the cement opening 130 to impregnate the intramedullary implant 100 with cement to enhance bone fixation.

The main opening 115 can lead to a first chamber 185 having a first longitudinal central axis. The cement opening 130 can lead to a second chamber 190 having a second longitudinal central axis, wherein the second chamber 190 can be configured to retain cement to enhance bone fixation. The first chamber 185 can be defined by the main opening 115 (e.g. a first end portion of the first chamber 185) and the first wall structure 187, wherein the first wall structure 187 resides at a second end portion of the first chamber 185. The second chamber 190 can be defined by the cement opening 130 (e.g. a first end portion of the second chamber 190) and the second wall structure 192, wherein the second wall structure 192 resides at a second end portion of the second chamber 190. The second longitudinal central axis can be eccentric with respect to the first longitudinal central axis, such that the first chamber 185 can be shifted from or offset with respect to the second chamber 190. In some cases, the first chamber 185 can be parallel to the second chamber 190 as to be aligned with the bone structure, such as the femur.

The midsection 194 of the proximal femoral replacement component 110 can resides between the first wall structure 187 and the second wall structure 192, the first aperture 120a and the second aperture 120b, and/or the first chamber 185 in contact with the second chamber 190. The midsection 194 can define a joint between the first chamber 185 and the second chamber 190. The midsection 194 can include a passage 195 between the chambers 185/190 to provide fluid communication extending from the first aperture 120*a* to the second aperture 120*b*. The passage can have a diameter similar to the diameters of the bolt apertures 120*a*/120*b* The passage 195 can be tapered based on the diameter of the bolt aperture 120*a*/120*b*. The passage providing fluid communication can pass the cement injected into the second chamber 190 via the cement opening 130 to at least a portion of the first chamber 185 to enhance bone fixation. The first wall structure 187 can include the second aperture 120*b* formed therein, wherein the bolt receiver 125 can extend from the second aperture 120*b* residing in the first wall structure 187. The second wall structure 192 can include the first aperture 120*a* formed inside the said structure 192, allowing the side locking bolt 180 to be inserted.

In some embodiments, the passage of the midsection 194 can be walled or blocked by the insertion of the nail component 150. In some other embodiments, the passage of the midsection 194 can be walled or blocked via insertion of the side locking bolt 180 passing through the first aperture 120*a*, the nail bolt aperture 165, and the second aperture 120*b* to secure the nail component 150 within the proximal femoral replacement component 110. The side locking bolt 180 can be further secured by the cement injected via the cement opening 130. In some cases, the proximal femoral replacement component 110 does not have the cement opening 130 such as to secure the side locking bolt 180 via an engagement feature residing in the bolt receiver 125 without cement injection.

Referring back to FIGS. 1A, 1B, 1C, 1D, 1E, and 1F, the intramedullary implant 100 can be inserted and secured in the femur, the pelvis, or other bone structures (e.g. clavicle, humerus, ulna, etc.) to align, stabilize, and repair the structural integrity of a fractured, separated, or otherwise damaged bone structure. One of two choices can be made for internal fixation including a load-bearing (prosthesis) and a load-sharing device, wherein the nail implant can easily be converted into a load-bearing for internal fixation. The method described herein refers specifically to repairing the femur via the load-bearing pelvis, however, it is to be noted that the embodiments of the intramedullary implant 100 are not limited to the said bone structure, but can be implemented between, for example, the scapula and the humerus.

For inserting the nail component, a surgeon can access a medullary canal at a first end portion of the femur. The medullary canal can be referred to as a cavity of the bone structure, which can be accessed via incision of the femur, so as to expose the proximal femur as necessary. The exposure of the proximal femur can identify the recurrent disease by a standard lateral approach for exposing the hip joint. The femur can be separated from the femoral necking connecting the femur to the pelvis to expose the medullary canal of the femur.

The surgeon can insert the nail component via the medullary canal subsequent to exposing the medullary canal of the femur. The medullary canal can extend from the first bone end portion (e.g. the top of the femur) to a second bone end portion of the femur (e.g. the bottom of the femur). The insertion of the said component can travel from the first bone end portion to a distance from the second bone end portion, wherein the component concurrently aligns the plurality of femur portions.

The alignment of the nail bolt aperture can be determined by the surgeon based on the longitudinal axis of the femoral neck connecting to the pelvis. The alignment can be further determined based on the bolt aperture of the proximal femoral replacement component 110, such that the side locking bolt can travel through the first aperture of the bolt aperture, the nail bolt aperture, and the second aperture of the bolt aperture. The surgeon can twist or turn the nail component to position the alignment of the nail bolt aperture subsequent to determining the alignment.

The surgeon can determine to couple the proximal femoral replacement component 110 with the nail component via accessing the medullary canal at the first bone end portion of the femur. The proximal femoral replacement component can be coupled with the nail component via the main opening, wherein the main opening leads to the first chamber. The first chamber can be tapered so as to friction fit the nail component to the first chamber. The bolt receiver of the proximal femoral replacement component can be inserted to a medullary canal of the femoral neck to secure with the pelvis, such that the femur can be coupled to the femoral neck.

In some cases, the surgeon can determine to insert the bolt receiver of the proximal femoral replacement component through the femoral neck to secure with the pelvis, prior to engaging with the nail component. The main opening can then be secured with the nail component subsequent to securing the proximal femoral replacement component with the pelvis. The femur can be coupled with the femoral neck and the pelvis subsequent to securing the said components.

The surgeon can drill an insert aperture adjacent to the first aperture of the bolt aperture corresponding to the nail bolt aperture and the second aperture of the bolt aperture, as to insert the side locking bolt. The side locking bolt can be then be inserted and secured to the bolt receiver via at least friction fit and/or the engagement feature of the bolt receiver. The side locking bolt can be easily replaced, if necessary, to convert from the nail implant to a load bearing hip replacement.

The cement opening of the proximal femoral replacement component can be accessed via a surgical hole or a gap in the bone structure. The surgeon can insert a long nozzle of the cement injector into the cement opening as desired to maximize distal and/or proximal fixation (see description above). The cement proportion can be injected as clinically indicated to secure the side locking bolt, engaged to the bolt receiver, to the proximal femoral replacement component. The cement can be injected so as to create a monoblock, wherein the side locking bolt can be engaged with the monoblock of cement and the bolt receiver for additional security.

To implant the disclosed intramedullary nail, the surgeon may expose as necessary the proximal femur to identify the recurrent disease by a standard lateral approach. Then the cephalic screw should be removed and the cancer then excised as clinically indicated. Based on the type of excision, high-speed burr can be used to prepare the proximal femur by removing bone as necessary to slide the proximal component, while at the same time preserving the gluteal insertion as much as possible. Once prepared, the long nozzle of the cement injector can be inserted in the nail as desired to maximize distal and/or proximal fixation (see description above). The proximal femoral component can then be trialed as necessary and ultimately locked in through the same screw hole of the nail cephalic screw using the locking bolt. Bone cement can then be added proximally to interlock the construct by creating a monoblock. Then a bipolar component can be trialed over the morse taper to match the patient's hip center of rotation, offset and limb length.

To convert the nail implant to a load bearing hip replacement, an effort should be made to assess stability of the implant and possibly inject distal and/or proximal cement as needed. If the hip need to be converted in a total hip replacement, an acetabular component is then needed to address fixation as necessary based on extent and geometry of bone loss.

Additional non-limiting features and details can be found in the Appendix.

Non-limiting examples of various embodiments are disclosed herein. Features from one embodiments disclosed herein may be combined with features of another embodiment disclosed herein as someone of ordinary skill in the art would understand.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of apparatuses or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way unless otherwise specifically noted. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. An intramedullary fixation system comprising:
a proximal femoral replacement component including a first opening and a first aperture and a second aperture separated from the first aperture via the first opening;
a nail component configured to be insertable within a medullary cavity of a bone and extending from a first nail end portion to a second nail end portion, the second nail end portion including a channel, the second nail end portion sized to be received within the first opening of the proximal femoral replacement component, the channel configured to be aligned with the first aperture and the second aperture of the proximal femoral replacement component when the second nail end portion is received within the first opening; and
a side locking fixation component extending from a first end portion to a second end portion, the second end portion configured to pass through the first aperture of the proximal femoral replacement component, the channel of the nail component, and the second aperture of the proximal femoral replacement component to secure the nail component to the proximal femoral replacement component,
wherein the second aperture of the proximal femoral replacement component defines an opening of a fixation component receiver, the fixation component receiver configured to secure the second end portion of the side locking fixation component subsequent to the side locking fixation component passing through the first aperture of the proximal femoral replacement component, the channel of the nail component, and the second aperture of the proximal femoral replacement component, wherein the first aperture and the second aperture have diameters such that the side locking fixation component can be inserted via the first aperture and/or the second aperture interchangeably.

2. The system of claim 1, wherein the fixation component receiver extends from the proximal femoral replacement component at an angle with respect to a longitudinal axis of the proximal femoral replacement component.

3. The system of claim 1, wherein the proximal femoral replacement component further comprises a first end portion defining the first opening having a first longitudinal central axis and a second end portion defining a second opening having a second longitudinal central axis, the second longitudinal central axis being eccentric with respect to the first longitudinal central axis.

4. The system of claim 1, wherein the proximal femoral replacement component comprises a first chamber defined by the first opening at a first end portion of the first chamber and a first wall structure at a second end portion of the first chamber and including the second aperture; and
a second chamber defined by a second opening at a first end portion of the second chamber and a second wall structure at a second end portion of the second chamber and including the first aperture, the first chamber and the second chamber being in fluid communication via a passage extending from the first aperture to the second aperture.

5. The system of claim 1, further comprising a fixation component receiver protruding from a sidewall of the proximal femoral replacement component, the fixation component receiver extending from a receiver first end to a receiver second end, wherein the fixation component receiver tapers from the receiver first end to the receiver second end.

6. The system of claim 1, wherein the side locking fixation component has an external diameter sized to match an internal diameter of a fixation component receiver extending from the proximal femoral replacement component.

7. The system of claim 1, wherein the second end portion of the side locking fixation component is configured to lockably engage with a corresponding fixation component receiver extending from the proximal femoral replacement component.

8. The system of claim 1, wherein:
a length of the nail component is at least four times a length of the proximal femoral replacement component; or
a diameter of the first aperture and the second aperture of the proximal femoral replacement component is at least four times less than a diameter of the first opening of the proximal femoral replacement component.

9. A proximal femoral replacement component comprising:
a first opening configured to receive a nail end portion of a nail component, the nail end portion including a channel configured to be aligned with a first aperture and a second aperture when the nail end portion is received within the first opening; and
a fixation component receiver extending from the proximal femoral replacement component at an angle with respect to a longitudinal axis of the proximal femoral replacement component;
wherein the second aperture is separated from the first aperture via the first opening, wherein the proximal femoral replacement component is configured to receive a side locking fixation component through the first aperture, the channel of the nail component, and the second aperture to secure the nail component to the proximal femoral replacement component, wherein the second aperture of the proximal femoral replacement component defines an opening of the fixation component receiver, the fixation component receiver configured to secure the side locking fixation component subsequent to the side locking fixation component passing through the first aperture of the proximal femoral replacement component, the channel of the nail component, and the second aperture of the proximal femoral replacement component, and wherein the first aperture and the second aperture have diameters such that the side locking fixation component can be inserted via the first aperture and/or the second aperture interchangeably.

10. The component of claim 9, further comprising a first end portion defining the first opening having a first longitudinal central axis and a second end portion defining a second opening having a second longitudinal central axis, the second longitudinal central axis being eccentric with respect to the first longitudinal central axis.

11. The component of claim 9, further comprising:
a first chamber defined by the first opening at a first end portion of the first chamber and a first wall structure at a second end portion of the first chamber and including the second aperture; and
a second chamber defined by a second opening at a first end portion of the second chamber and a second wall structure at a second end portion of the second chamber and including the first aperture, the first chamber and the second chamber being in fluid communication via a passage extending from the first aperture to the second aperture.

12. The component of claim 9, wherein a diameter of the first aperture and the second aperture is at most one fourth a diameter of the first opening; and
wherein a length of the nail component is at least four times a length of the proximal femoral replacement component.

13. A method for implanting intramedullary nails using an intramedullary fixation system, comprising the steps of:
accessing, by an incision, a medullary canal at a first end portion of a bone;
inserting, via the medullary canal from the first bone end portion to a distance from a second bone end portion, a nail component extending from a first nail end portion to a second nail end portion, the second nail end portion including a channel;
determining the alignment of the channel of the second nail end portion respective to a first aperture and a second aperture of a proximal femoral replacement component;
aligning, subsequent to determining the alignment of the channel, the channel of the second nail end portion respective to the first aperture and the second aperture of the proximal femoral replacement component;
inserting, via the medullary canal at the first bone end portion, the proximal femoral replacement component including the first opening and the first aperture and the second aperture separated from the first aperture via the first opening;
encapsulating, by the proximal femoral replacement component, the second nail end portion; and
inserting, via a portion of the bone corresponding to the channel and the first aperture and the second aperture, a side locking fixation component through the first aperture of the proximal femoral replacement component, the channel of the nail component, and the second aperture of the proximal femoral replacement component to lock the proximal femoral replacement component and the nail component to the bone.

14. The method of claim 13, wherein the second aperture of the proximal femoral replacement component defines an opening of a fixation component receiver, the fixation component receiver configured to secure the second end portion of the side locking fixation component subsequent to the side locking fixation component passing through the first aperture of the proximal femoral replacement component, the channel of the nail component, and the second aperture of the proximal femoral replacement component.

15. The method of claim 14, wherein the proximal femoral replacement component includes a first chamber defined by the first opening at a first end portion of the first chamber and a first wall structure at a second end portion of the first chamber, the second aperture being formed in the first wall structure; and
wherein the fixation component receiver extends from the second aperture in the first wall structure.

16. The method of claim 13, wherein the fixation component receiver extends from the proximal femoral replacement component at an angle with respect to a longitudinal axis of the proximal femoral replacement component.

17. The method of claim 13, wherein the proximal femoral replacement component further comprises a first end portion defining the first opening having a first longitudinal central axis and a second end portion defining a second opening having a second longitudinal central axis, the second longitudinal central axis being eccentric with respect to the first longitudinal central axis.

18. The method of claim 13, wherein the proximal femoral replacement component comprises a first chamber defined by the first opening at a first end portion of the first chamber and a first wall structure at a second end portion of the first chamber and including the second aperture; and
a second chamber defined by a second opening at a first end portion of the second chamber and a second wall structure at a second end portion of the second chamber and including the first aperture, the first chamber and the second chamber being in fluid communication via a passage extending from the first aperture to the second aperture.

\* \* \* \* \*